US00PP11819P2

(12) United States Plant Patent
Kent

(10) Patent No.: US PP11,819 P2
(45) Date of Patent: Mar. 20, 2001

(54) BROMELIAD PLANT NAMED 'GUZ 207'

(76) Inventor: Jeffrey C. Kent, 2074 Pleasant Heights, Vista, CA (US) 92084

( * ) Notice: Subject to any disclaimer, the term of this patent is extended or adjusted under 35 U.S.C. 154(b) by 0 days.

(21) Appl. No.: 09/114,404

(22) Filed: Jul. 13, 1998

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,945 * 7/1997 Rabin ..... Plt./371

* cited by examiner

*Primary Examiner*—Bruce R. Campell
*Assistant Examiner*—Wendy A Baker

(57) ABSTRACT

A Guzmania hybrid having floral bracts with a color combination of reddish purple and orange red, and a somewhat compact inflorescence.

1 Drawing Sheet

BACKGROUND OF THE INVENTION

This application relates to a newly developed interspecific hybrid Guzmania plant resulting from a planned breeding program that I conducted on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants which will be attractive to the consumer; which will develop reasonably rapidly under controlled conditions; and, retain for a long term, highly attractive and bright inflorescence; i.e., bract coloration; after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the art-tissue culture methods while continuing the distinctive characteristics of the plants through progressive clonal generations.

The plant of this disclosure was a selection from the progeny resulting from the cross of *Guzmania lingulata* 'Panama Red' (unpatented)×*Guzmania wittmackii*, 'Equador Medium Pink' (unpatented). With the recognition that this seedling from the cross satisfied the objects of the breeding program, the individual was isolated and set aside for further observation and testing. The resulting selection has been assigned the designation 'GUZ 207' for purposes of identification. This plant has been reproduced by tissue culture at Apopka, Fla. and elsewhere, and the clonal specimens resulting have been determined to be identical to the original selection in all distinguishing characteristics. The superior attributes of this plant will be revealed in the botanical description to follow.

SUMMARY OF THE INVENTION

The attributes of the plant 'GUZ 207' which distinguish it from the other similar Guzmania hybrids are described as follows:

The inflorescence is a branched spike of reddish purple and orange red in overall appearance. The scape bracts are linear acute, reddish purple on the obverse and reverse. Both sides of the lower scape bract tips blend into orange red while both sides of the upper bract tips blend into more pronounced purplish red. The floral scape is lanceolate, translucent at the base with dark red purple lineations becoming solid purple red toward the middle and blending into orange red at the tips.

The leaves are medium size, acuminate and acutely pointed, medium green in color on both sides, with red purple staining and lineation toward the bases.

This medium sized Guzmania has an inflorescence in a color combination not commonly seen in cultivation. Usually the colors in scape bracts are confined to the same color group, and are not as subtly blended. Some compact characteristics of the inflorescence seem to be derived from the seed parent *Guzmania lingulata* 'Panama Orange'. The reddish purple and orange red color also seems to come from the seed parent. Some height and color comes from the pollen parent. *Guzmania wittmackii* 'Ecuador Medium Pink' is quite tall compared to other *wittmackii*and appears to impart more height than other *lingulata wittmackii* crosses. The rich bright medium pink of the *wittmackii*appears to darken the bract color of the crosses. It is a sterile F 1 hybrid which remains in color under dim light, indoors for 2½ to 3 months.

BRIEF DESCRIPTION OF THE DRAWING

The single color photograph of the drawing depicts a mature specimen of the plant in mid to late flowering stage. Illustrated are the mature leaves, scape bract and floral bract. The color definitions in the specification have been taken from The R.H.S. Colour Chart of The Royal Horticultural Society. While the colors depicted are believed to be of a high level of color fidelity, the coloration of this plant should be understood to be approximate, and somewhat variable as a function of cultural conditions and horticultural practices. For example, the bract color might slightly fade if the plant is subjected to bright light and the leaf color may vary depending on the composition and the concentration of fertilizer which may be applied to the plant.

It takes approximately a one year time period from liner to market.

BOTANICAL DESCRIPTION OF THE PLANT

Parentage:

*Seedling.*—Seed parent — *Guzmania lingulata* 'Panama Red'. Pollen parent — *Guzmania wittmacki* 'Ecuador Medium Pink'.

Propagation:

*Method of asexual reproduction.*—Tissue culture.

*Where reproduction took place.*—Twyford Plant Labs, 4051 Fudge Road, Apopka, Fla. 32703.

Plant: Monocot perennial Medium in size Overall Height from soil surface 18" to 20" including inflorescence Overall Width 24" Vigorous growth to anthesis relative to other Guzmania plants. This hybrid blooms in 15 months from transplant in comparison to earlier Guzmania hybrids that bloom in 17 months. Upright, spreading, dense, vase formed and tender. Leaves will be damaged at temperatures below 32° F., and entire plant will not survive exposure to temperatures below 32° F. for several hours.

Leaves:

*Length.*—20".

*Width.*—1¾".

*Number.*—28–31.

*Medium in size.*—Leaves arching to somewhat recurved. 143-A in color obverse and reverse, stained 57-A particularly toward the bases on the reverse with some lineation of 57-A. Lanceolate, narrowly acuminate, acutely pointed, medium thickness and smooth.

*Margin.*—Smooth.

Flower buds: Inflorescence a branched spike.

*Tender.*—Buds are destroyed at temperatures below 32° F.

*Length.*—2.5" to 3".

*Width.*—0.5 to 0.75".

Pointed. Appressed. Scape bracts linear acute 7"×1¾" at the base of inflorescence Decreasing to 3¼"×1" at the apex Color 57A on the obverse: 58-A on the reverse Scape bracts:

*Lower bracts.*—Lower third of bract- 57-A obverse and 58-A reverse. Middle third of bract blending to 51-A obverse and reverse. Upper third (tips) 143-A, 148-A reverse.

*Upper bracts.*—Lower third of bract 74-A obverse and reverse; Middle third of bract blending to 51-A obverse and reverse Upper third (tips) 143-A obverse and reverse Floral bracts:

*Lanceolate.*—2½" in length×½" wide. Lower third containing lineations 60-B obverse and reverse; Middle third blends to 74-A obverse and reverse; Upper third (tips) blend to 51-A obverse and reverse; some tips of floral bracts maintain green coloration 143-A obverse and reverse.

*Bracts.*—number: 17–20.

*Scape length.*—15"–18".

Flowers: Medium in size. Flowers apetiolate, corolla cylindrical, sepals ⅞"×3/16", 3 in number; 150-A in color. stained 51A at the base. Petals 1¼"×¼" 150-A in color; 3 in number. Scarcely open at anthesis; joined less then half the length from the base. Fruit is a three-celled capsule, splitting open longitudinally when mature Seeds with pappus seeds not viable.

What is claimed is:

1. A new and distinct variety of Guzmania plant named Guz 207 as illustrated and described characterized in that the inflorescence is in a color combination of reddish purple and orange red.

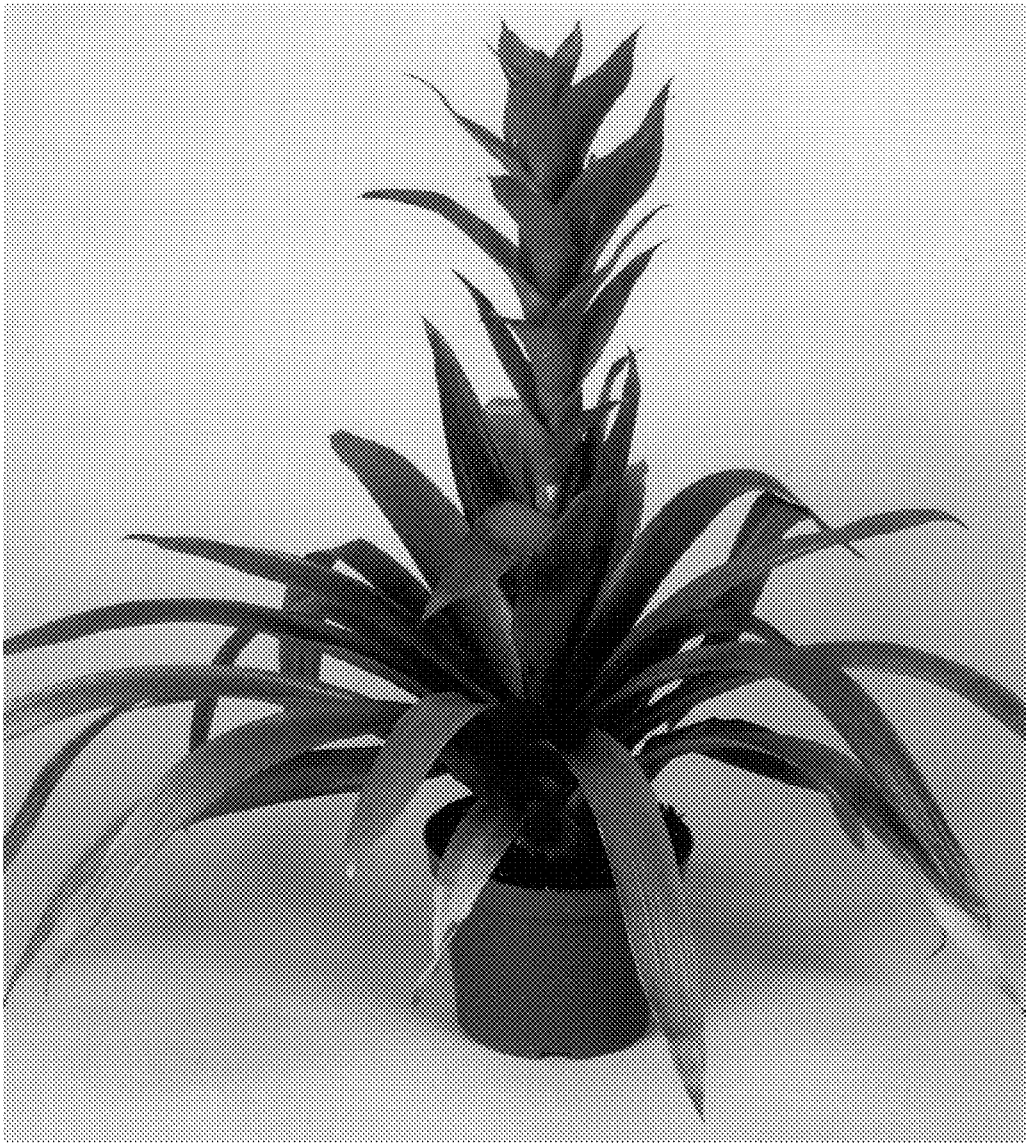

* * * * *